United States Patent
Förster

(10) Patent No.: US 6,499,996 B2
(45) Date of Patent: *Dec. 31, 2002

(54) JACKSCREW FOR USE IN CORRECTING MISALIGNMENTS OF TEETH

(76) Inventor: Rolf Förster, Westliche Karl-Friedrich-Str. 151, D-75172 Pforzheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/929,020

(22) Filed: Sep. 15, 1997

(65) Prior Publication Data

US 2002/0001789 A1 Jan. 3, 2002

Related U.S. Application Data

(63) Continuation of application No. PCT/EP96/01083, filed on Mar. 14, 1996.

(30) Foreign Application Priority Data

Mar. 15, 1995 (DE) .................................... 295 04 198 U
May 23, 1995 (DE) .......................................... 195 18 846

(51) Int. Cl.[7] ................................................ A61C 3/00
(52) U.S. Cl. ........................................................ 433/7
(58) Field of Search ............................................ 433/7

(56) References Cited

U.S. PATENT DOCUMENTS

| | | | | |
|---|---|---|---|---|
| 5,167,500 A | * | 12/1992 | Miura | 433/7 |
| 5,312,247 A | | 5/1994 | Sachdeva | 433/7 |

FOREIGN PATENT DOCUMENTS

| | | | | |
|---|---|---|---|---|
| CH | 283235 | * | 9/1952 | 433/7 |
| DE | 824832 | | 1/1951 | |
| DE | 29504198 | * | 7/1995 | 433/7 |

* cited by examiner

*Primary Examiner*—John J. Wilson

(57) ABSTRACT

Jackscrew for use in correcting misalignments of teeth, comprising two main bodies (1,2), whose mutual separation can be adjusted by means of a spindle (3) provided with an operating part (5) and, continuous with that part, one or two screw-thread sections (7,11) the operating part (5) being rotatably mounted in one body (1) and one screw-thread section (11) being rotatably mounted in the other body (2), further comprising straight-line guide elements (22,23) which engage with both bodies (1,2) and guide them in a straight line while also preventing any relative rotation when the separation between the bodies is altered, and a threaded sleeve (13,14) on each of the screw-thread sections (7,11) of the spindle (3) the threaded sleeve (13,14) being guided inside a recess (6,10) in the respective body (1,2) and along the spindle (3) so as not to rotate relative to the body and transmitting its sliding motion to the bodies (1,2) via a spring (18,19) which determines the expansion force. The spring (18,19) is made from a shape-memory alloy, which is pseudo-elastic at temperatures prevailing inside the mouth.

7 Claims, 2 Drawing Sheets

US 6,499,996 B2

JACKSCREW FOR USE IN CORRECTING MISALIGNMENTS OF TEETH

"This is a continuation of international application PCT/EP96/01083, filed Mar. 14, 1996 which designated the United States and is now abandoned."

BACKGROUND OF THE INVENTION

The present invention relates to a jackscrew for use in correcting misalignments of teeth, comprising two main bodies. A jackscrew of this kind is known from German Patent 824 832. The known jackscrew serves, in conjunction with a split palate plate, to effect a correction into the correct tooth position in the event of an incorrect tooth position, for example if teeth in the upper or lower jaw project into the oral cavity or are displaced laterally inward. The two parts of the palate plate are spanned by the jackscrew and forced apart by adjusting the jackscrew. For this purpose, the known jackscrew has two bodies whose spacing relative to one other can be varied by means of a double spindle. Each of these bodies is usually embedded in one of the palate plates. The pressure which is built up by actuation of the spindles is cushioned by compression springs which act between the spindles and the two bodies that are to be forced apart. In the case of the known jackscrew, the springs are helical springs which surround the two threaded sections of the spindle and are braced at their one end against a cover which closes off a recess of the respective body so as to brace at their other end against a buttress in the form of a threaded sleeve which is threaded onto the relevant threaded section of the spindle and, secured against rotation, is displaced in the relevant recess of the body upon actuation of the spindle. A disadvantage in this context is the fact that in accordance with Hooke's law, the spring force weakens as the treatment progresses. As a result, the effectiveness of the jackscrew also weakens during the course of the treatment, and the tooth position correction slows down and comes entirely to a standstill whenever the jackscrew is not readjusted. To avoid the need for frequent readjustment of the jackscrew, it is easy to give in to the temptation to load the springs in the jackscrew more strongly than is good for the teeth and the tooth position.

With the known jackscrew, it was moreover possible for deposits of food residues and tartar to penetrate into the jackscrew and cause jamming and immobilization of the screw.

It is the object of the present invention to indicate a way to make such jackscrews easier to work with, it being desirable on the one hand not to need to readjust the jackscrew so often, but on the other hand not to create the risk of shear stress peaks on the teeth.

SUMMARY OF THE INVENTION

This object is achieved by means of a jackscrew comprising two main bodies whose mutual separation is adjustable by means of a spindle provided with an operating part, and continuous with that part, one or two screw-thread sections, the operating part being rotatably mounted in one body, and one screw-thread section being rotatably mounted in the other body, further comprising straight-line guide elements which engage with both bodies and guide them in a straight line while also preventing any relative rotation when the separation between the bodies is altered, and a thread sleeve on each of the screw-thread sections of the spindle, the threaded sleeve being guided inside a recess in the respective body and along the spindle so as not to rotate relative to the body and transmitting its sliding motion to the bodies via a spring which determines the expansion force, characterized in that the spring is made from a shape-memory alloy which is pseudo-elastic at temperatures prevailing inside the mouth. The new jackscrew uses as the spring not a conventional steel spring but a spring made of a shape memory alloy that is pseudoelastic at the temperatures prevailing in the mouth. Preferred shape memory alloys are alloys based on nickel and titanium, in which nickel and titanium are contained in approximately equal atomic percentages. Alloys of this kind can exist, depending on the temperature selected, in either the austenitic or martensitic state. Martensite is present at lower temperatures, austenite at higher temperatures. The temperature at which the alloy begins to convert, upon cooling, from austenite into martensite is also referred to as the Ms point. In the martensitic state below the Ms point, alloys of this kind can exhibit shape memory: a plastic deformation occurring in the martensitic state can be reversed above the Ms point. A shape memory alloy of this kind can exhibit pseudoelastic behavior in a temperature range just above the Ms point. Pseudoelastic behavior is characterized in that the force required for an increasing elongation initially rises sharply as expected for an austenite, but then, after reaching an elongation of approximately 1 to 2%, increases only slightly as elongation progresses, and rises steeply again only after greater elongations (of 6 to 8%) are attained. The middle elongation region is referred to as the "martensite plateau." The name derives from the fact that martensite forms in the alloy in response to the tensile stress. When tension on the material is relaxed, it returns to the austenitic state. These pseudoelastic elongations are reversible to a large extent up to elongations greater than 6 to 8%. Because of the pronounced martensite plateau, pseudoelasticity does not obey Hooke's law. As a result, springs which behave in this pseudoelastic fashion are particularly suitable for the purposes of the present invention, since for spring travels in the martensite plateau range, the return force of the spring is almost independent of the spring travel. A jackscrew according to the invention thus has the great advantage that tensile stress remains almost unchanged over the course of the treatment. Because of the consistent spring load, the teeth are aligned more quickly than hitherto, and readjustment of the jackscrew is not required as often as in the existing art. Since there is almost no change in the spring force as long as it remains within the martensite plateau, it is moreover possible, by applying the invention, to reliably prevent an orthodontist from inadvertently applying excessive loads during a treatment, since simply by matching the spring travel to the elongation load of the jackscrew, it is possible to prevent any displacement beyond the martensite plateau from occurring; as a result, in the case of the jackscrew according to the invention, the tensile force is approximately determined only by the selection of the pseudoelastic spring, but not by the displacement travel of the spindle. The displacement travel of the spindle determines only the end of the tooth correction, not the force applied for it.

The invention makes the jackscrew substantially more convenient and reliable to use.

Pseudoelastic springs are known per se, but have hitherto not been used in jackscrews for orthodontic purposes, for which, according to the invention, they open up a substantially expanded field of application, putting an end once and for all to the hazards (damaging load peaks) associated with frequent readjustment of the jackscrew as required in the existing art.

Depending on the selected arrangement of the springs in the bodies of the jackscrew, the springs can be utilized as tension springs or compression springs. In terms of the construction of the jackscrew, an embodiment as compression springs is more favorable and therefore preferred.

The jackscrew could have a spindle with a head and a threaded portion, the head being mounted in a body and the threaded portion extending into the other body. Preferably, however, the spindle has two threaded portions which extend in opposite directions from an actuating member, located in the center, of the spindle, and have threads running in opposite directions. A configuration of this kind allows greater displacement travels.

In order to be effective, the spring must engage on the one hand on the body and on the other hand on the threaded sleeve located on the spindle. For this purpose, the recess in the body in which the threaded portion of the spindle, the threaded sleeve, and the spring are located is closed off by a cover whose installation completes assembly of the jackscrew. Said cover can be welded or soldered to the respective body, but it can also be pressed or set in and fastened by crimping over a rim provided on the body. Said cover then serves not only as a buttress for the spring, but also closes off the recess provided in the body at one end, so that food residues cannot penetrate from there, solidify, and thereby impair the function of the jackscrew. In order to prevent any penetration of food residues from the other side as well, a seal is preferably provided there, in particular an O-ring, which is arranged on the actuation member of the spindle in the vicinity thereof, and seals the access leading into the respective recess of the body from that end. If deposits of this kind, due to food residues, tartar, and accumulated plaque, are kept out of the recess in which the threaded sleeve and the pseudoelastic sleeve are located, proper functioning of the jackscrew throughout the course of the treatment can be ensured with no need for occasional cleaning operations to be performed.

The linear guide means are advantageously pins that are fixed in one of the two bodies and extend into bores of the other body. There is a certain risk of incrustation in the case of the linear guide means as well, although it is less than in the region of the spindle because the pins must slide out of the bores in which they are guided as the jackscrew is extended, but need not move inward; the pins also move back into the bores only over the length of the spring travel. It may nevertheless be advantageous to provide sealing rings there as well, which surround the pins and prevent the penetration of initially liquid food residues into the bores of the one body.

An exemplifying embodiment of the invention is shown in the attached drawings.

Figure 1:
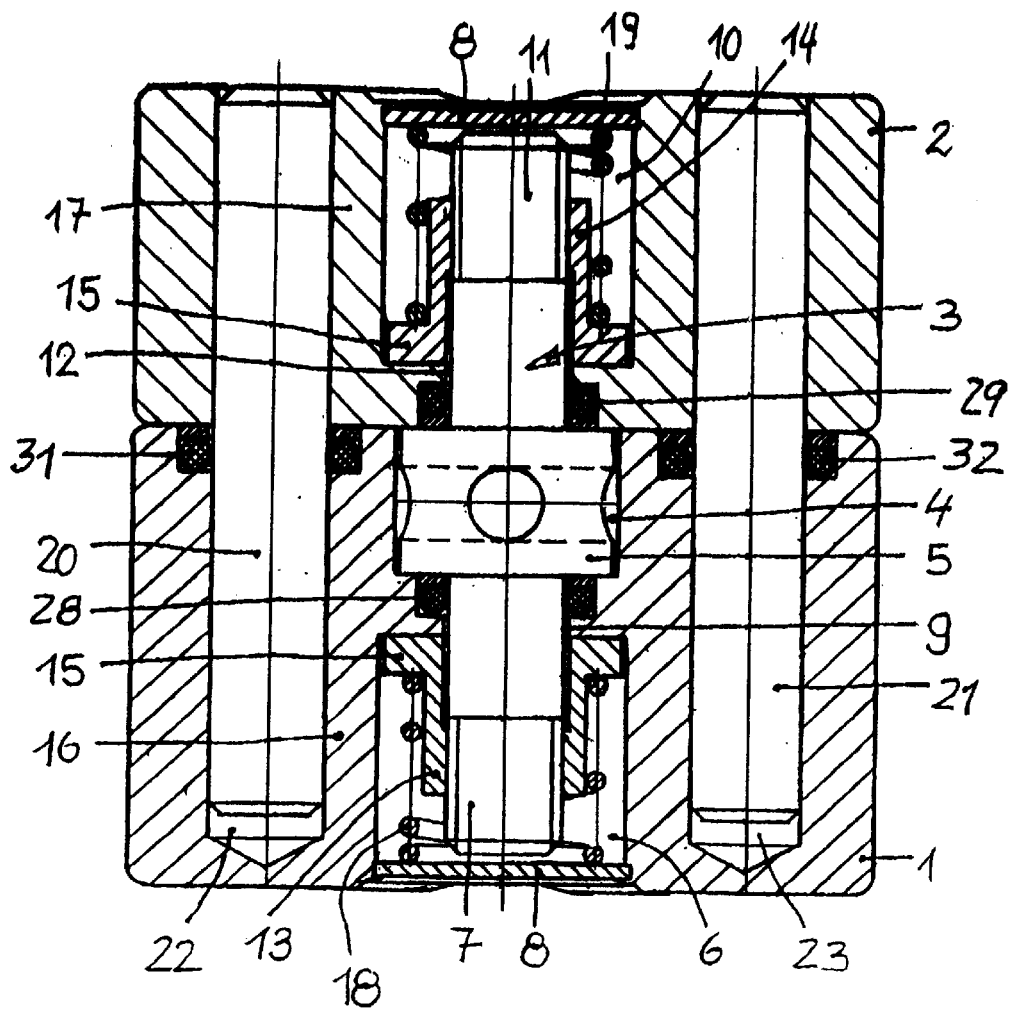
FIG. 1 shows a longitudinal section through a jackscrew.
Figure 2:
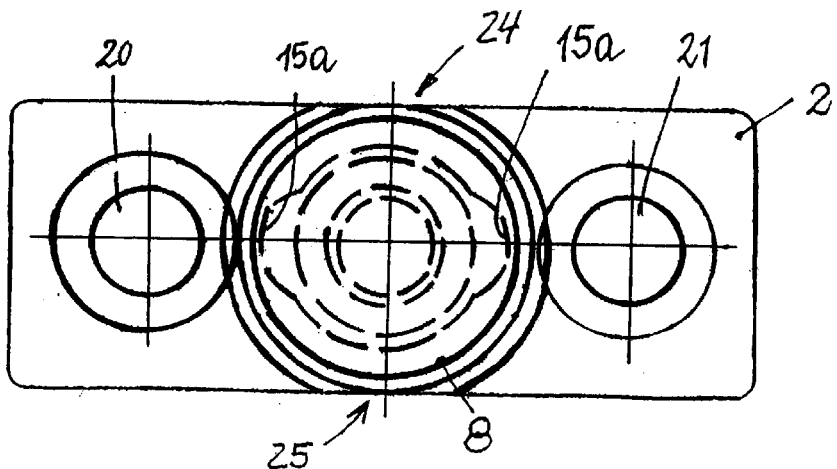
FIG. 2 shows an end view of the jackscrew.

The jackscrew shown in FIGS. 1 and 2 has two approximately parallelepipedal bodies 1 and 2, the spacing between which can be modified and which can be displaced by means of a spindle 3. For this purpose, the larger body 1 has a first recess 4 to receive a first threaded section 7 of the spindle. First recess 4 is located on the side facing second body 2, and is open in that direction. Second recess 6 is located on the opposite side of body 1 and is closed off by a cover 8. The two recesses 4 and 6 are joined by a cylindrical bore 9 through which passes the one threaded portion 7 of the spindle.

DETAILED DESCRIPTION OF THE INVENTION

The other body 2 has on its side facing first body 1 a recess 10, identical to recess 6, to receive a second threaded portion 11 of the spindle. Recess 10 is also closed off by a cover 8; on the side opposite it, body 2 has a cylindrical bore 12 through which threaded portion 11 passes into recess 10. In recesses 6 and 10, there is set on threaded portions 7 and 11 a respective threaded sleeve 13 and 14 which has a collar 15 with diagonal extensions 15a which engage into corresponding longitudinal guide grooves in walls 16 and 17 delimiting recesses 6 and 10, respectively, and prevent any rotation of threaded sleeves 13 and 14. A respective coiled spring 18 and 19 is clamped between collar 15 and cover 8.

Provided as linear guide means are two guide pins 20 and 21 which are pressed at their one end into bores of body 2 and moreover extend into bores 22 and 23 of body 1 and are displaceable therein.

The jackscrew is adjusted by engaging with a pin, from the open top surface 24 or from the open bottom surface 25, into one of the holes of the actuating member, and rotating it. This pushes threaded sleeves 13 and 14 away from one another, thereby loading coiled springs 18 and 19 which in turn, with the spring force available to them, move bodies 1 and 2 away from one another. O-rings 28 to 32 prevent food residues from penetrating into bores 22 and 23 or into recesses 6 and 10.

Figure 3:
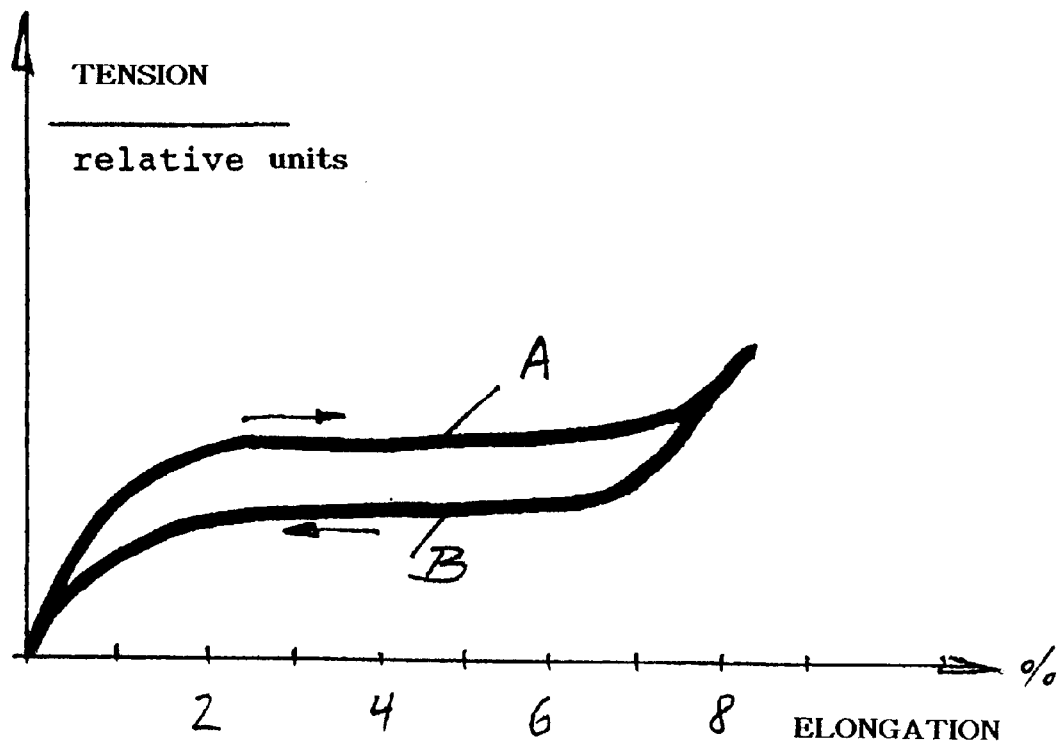
FIG. 3 shows a typical tension-elongation diagram for a pseudoelastic wire.

FIG. 3 shows a typical tension-elongation diagram for a pseudoelastic nickel-titanium wire. When a wire of this kind is elongated in tension, a moderately steeply rising tensile force is initially needed to continue elongating the wire. Above an elongation of approximately 2%, the tensile force necessary for continued elongation rises only very slightly, and then once again begins to rise more steeply at about 8% elongation (top branch A of the curve). If the wire is then released, the elongation relaxes along lower branch B of the curve. The phenomenon thus exhibits hysteresis. The flat portion of the characteristic curve, between 2% and 8% in the example shown (called the "martensite plateau"), is utilized for purposes of the invention. The rising portion of the curve between 0 and approximately 2% elongation, which is less effective for tooth correction, can be deactivated for tooth correction purposes by installing springs 18 and 19 into recesses 6 and 10 with a corresponding preload, and then closing off recesses 6 and 10 by, for example, crimping or welding cover 8.

[FIG. 3]

ZUG=TENSION relative . . . =Relative units

DEHNUNG=ELONGATION

What is claimed is:

1. Jackscrew for use in correcting misalignments of teeth, comprising two main bodies (1,2), whose mutual separation is adjustable by means of a spindle (3) provided with an operating part (5) and, continuous with that part, one or two screw-thread sections (7,11) the operating part (5) being rotatably mounted in one body (1) and one screw-thread section (11) being rotatably mounted in the other body (2), further comprising straight-line guide elements (22,23) which engage with both bodies (1,2) and guide them in a straight line while also preventing any relative rotation when the separation between the bodies is altered, and a threaded sleeve (13,14) on each of the screw-thread sections (7,11) of the spindle (3) the threaded sleeve (13,14) being guided inside a recess (6,10) in the respective body (1,2) and along the spindle (3) so as not to rotate relative to the body and transmitting its sliding motion to the bodies (1,2) via a spring (18,19) which determines the expansion force, characterized in that the spring (18,19) is made from a shape-memory alloy which is pseudo-elastic at temperatures prevailing inside the mouth.

2. Jackscrew as in claim 1 characterized in that the spring (18,19) consists of an alloy on the basis of nickel and titanium containing nickel and titanium in approximately equal atomic percentages.

3. Jackscrew as in claim 1 characterized in that the spring (18,19) is a compression spring.

4. Jackscrew as in claim 1 characterized in that the spindle has two screw-thread sections (7,11) with opposing threads.

5. Jackscrew as in claim 3 characterized in that the spring (18,19) is fixed between an abutment (15) provided for being at the threaded sleeve (13,14) and a cover (8) closing the recess (6,10) in the body (1,2) at its exterior end.

6. Jackscrew for use in correcting misalignments of teeth, comprising two main bodies (1, 2), whose mutual separation is adjustable by means of a spindle (3) provided with an operating part (5) and, continuous with that part, one or two screw-thread sections (7, 11) the operating part (5) being rotatably mounted in one body (1) and one screw-thread section (11) being rotatably mounted in the other body (2), further comprising straight-line guide elements which engage with both bodies (1, 2) and guide them in a straight line while also preventing any relative rotation when the separation between the bodies is altered, and a threaded sleeve (13, 14) on each of the screw-thread sections (7, 11) of the spindle (3) the threaded sleeve (13, 14) being guided inside a recess (6, 10) in the respective body (1, 2) and along the spindle (3) so as not to rotate relative to the body and transmitting its sliding motion to the bodies (1, 2) via a spring (18, 19) which determines the expansion force, characterized in that the spring (18, 19) is made from a shape-memory alloy which is pseudo-elastic at temperatures prevailing inside the mouth; and the screw-thread sections (7, 11) of the spindle (3) are surrounded by a seal (28, 29) which seals an access (9, 12) leading from the operating part into the respective recess (6, 10) of the body (1, 2).

7. Jackscrew for use in correcting misalignments of teeth, comprising two main bodies (1,2), whose mutual separation is adjustable by means of a spindle (3) provided with an operating part (5) and, continuous with that part, one or two screw-thread sections (7, 11) the operating part (5) being rotatably mounted in one body (1) and one screw-thread section (11) being rotatably mounted in the other body (2), further comprising straight-line guide elements which engage with both bodies (1,2) and guide them in a straight line while also preventing any relative rotation when the separation between the bodies is altered, and a threaded sleeve (13,14) on each of the screw-thread sections (7, 11) of the spindle (3) the threaded sleeve (13, 14) being guided inside a recess (6, 10) in the respective body (1, 2) and along the spindle (3) so as not to rotate relative to the body and transmitting its sliding motion to the bodies (1, 2) via a spring (18, 19) which determines the expansion force, characterized in that the spring (18, 19) is made from a shape-memory alloy which is pseudo-elastic at temperatures prevailing inside the mouth; and the straight-line guide elements (20, 21) are pins which are fixed in one of the bodies (2) and extend into bores (22, 23) of the other body (1) being sealed by gaskets (31, 32) surrounding the pins (20, 21).

* * * * *